United States Patent [19]

Ávár

[11] Patent Number: 4,661,595

[45] Date of Patent: Apr. 28, 1987

[54] METHOD FOR PRODUCING XANTHONE AND THIOXANTHONE COMPOUNDS USEFUL AS PHOTOINITIATORS

[75] Inventor: Lajos Ávár, Biel-Benken, Switzerland

[73] Assignee: Sandoz Ltd., Basel, Switzerland

[21] Appl. No.: 753,634

[22] Filed: Jul. 10, 1985

[30] Foreign Application Priority Data

Jul. 12, 1984 [CH] Switzerland ............ 3388/84
Jul. 12, 1984 [CH] Switzerland ............ 3390/84

[51] Int. Cl.⁴ .............. C07D 491/052; C07D 515/04; C07D 335/16; C07D 319/00
[52] U.S. Cl. ......................... 546/89; 546/80; 549/27; 549/359; 549/387; 522/50; 522/53; 522/63
[58] Field of Search ............ 546/89, 80; 549/27, 549/359, 387; 522/53, 50, 63

[56] References Cited

U.S. PATENT DOCUMENTS 4,348,530 9/1982 Kvita et al. ............ 549/27
4,385,182 5/1983 Fischer et al. ............ 549/27

FOREIGN PATENT DOCUMENTS 0075607 4/1983 European Pat. Off. ............ 546/89
016537 8/1976 Japan ............ 546/89
0122785 9/1980 Japan ............ 546/89
2018243 10/1979 United Kingdom .
1595710 8/1981 United Kingdom .

OTHER PUBLICATIONS

Organic Chemistry of Sulfur, edited by S. Oae (1977), pp. 231–235.

Primary Examiner—John E. Kittle
Assistant Examiner—Cynthia Hamilton
Attorney, Agent, or Firm—Gerald D. Sharkin; Richard E. Vila; Thomas C. Doyle

[57] ABSTRACT

A method for preparing a compound of formula I

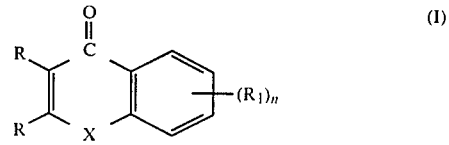

in which
X is O or S;
both groups R together with the two carbon atoms to which they are attached form a fused aromatic group;
$R_1$ is an organic radical; and
n is 0, 1, 2 or 3 comprising reacting a compound of formula II

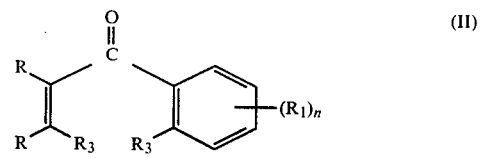

where R, $R_1$ and n are defined above and where each $R_3$, independently, is $C_{1-12}$alkoxy or one $R_3$ is $C_{1-12}$alkoxy and the other $R_3$ is halogen.

with elemental sulphur in an alkaline medium, a metal sulphide or a metal hydrosulphide.

Compounds of formula I and formula II are useful as photoinitiators.

20 Claims, No Drawings

METHOD FOR PRODUCING XANTHONE AND THIOXANTHONE COMPOUNDS USEFUL AS PHOTOINITIATORS

The invention relates to xanthone and thioxanthone compounds which can be used as photoinitiators.

According to the invention there is provided a method for preparing a compound of formula I

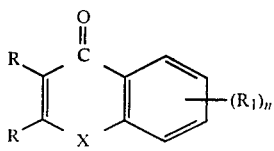

in which
X is O or S;
both groups R together with the two carbon atoms to which they are attached form a fused aromatic group;
$R_1$ is selected from $C_{1-18}$alkyl, cyclo$C_{5-7}$alkyl, phenyl $C_{1-4}$alkyl, $C_{1-4}$alkoxy $C_{1-4}$alkyl, $C_{1-4}$alkoxycarbonyl $C_{1-4}$-alkyl, $C_{1-4}$alkylcarbonyloxy $C_{1-4}$alkyl, $C_{1-8}$alkoxy, phenyl $C_{1-4}$-alkoxy and halogen; and
n is 0, 1, 2 or 3
comprising reacting a compound of formula II

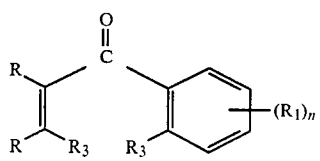

where
R, $R_1$ and n are defined above and where each $R_3$, independently, is $C_{1-12}$alkoxy or one $R_3$ is $C_{1-12}$alkoxy and the other $R_3$ is halogen,
with elemental sulphur in an alkaline medium, a metal sulphide or a metal hydrosulphide.

In this Specification the significances of any symbol appearing more than once in a formula are independent of one another, unless indicated to the contrary.

Preferably halogen is chlorine or bromine.
Preferably an alkyl present is $C_{1-4}$alkyl.
Preferably any alkali metal present is sodium or potassium.

When each $R_3$, independently, is $C_{1-12}$alkoxy, the compounds of formula I formed are those where X is O and where one $R_3$ is $C_{1-12}$alkoxy and the other $R_3$ is halogen, compounds of formula I formed are those in which X is S. However, in the latter case up to 20% of the product formed may be the corresponding compound of formula I in which X is O.

Preferred compounds of formula I which can be prepared by the method according to the invention are of formula Ia

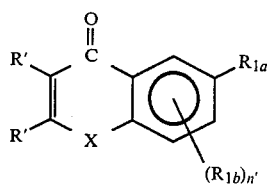

in which
X is O or S, preferably S;
$R_{1a}$ is hydrogen, $C_{1-18}$alkyl, phenyl $C_{1-3}$alkyl, cyclo$C_{5-7}$alkyl (preferably cyclohexyl), $C_{1-8}$alkoxy, benzyloxy, $C_{1-3}$alkoxycarbonylethyl or halogen;
$R_{1b}$ is $C_{1-8}$alkyl, $C_{1-8}$alkoxy or halogen;
n' is 0, 1 or 2;
both groups R' together with the two carbon atoms to which they are attached form

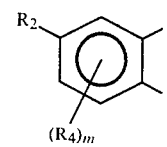

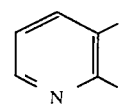

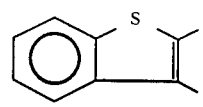

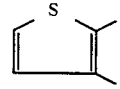

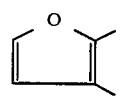

where
$R_2$ is hydrogen, $C_{1-4}$alkyl, $C_{1-4}$alkoxy or halogen;
$R_4$ is $C_{1-4}$alkyl or halogen provided not more than one $R_4$ group is halogen; and
m is 0, 1, 2 or 3.

Preferred compounds of formula II are of formula IIa

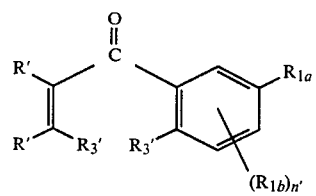

in which
R', $R_{1a}$, $R_{1b}$ and n' are defined above and each $R_3'$ independently is $C_{1-6}$alkoxy; or
one $R_3'$ is $C_{1-6}$alkoxy and the other $R_3'$ is Cl or Br.

The compounds of formula II and IIa can be prepared by known metods from known compounds, for example, by the reaction of an acid chloride of formula III

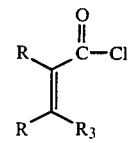

with a compound of formula IV

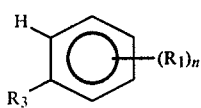

where all the symbols are defined above, under water-free conditions in the presence of AlCl₃ (Friedel-Craft's reaction).

The xanthones (i.e. compound of formula I in which X is O) and in particular the thioxanthones (i.e. compounds of formula I in which X is S) are known to be useful as photoinitiators. It has now been found that the compounds of formulae II and IIa are also good photoinitiators.

Preferably in the method according to the invention compounds of formula II are reacted with elemental sulphur in an alkaline medium or with a metal sulphide.

In the method according to the invention in which a metal sulphide is used, the metal sulphide is preferably an alkali metal or alkaline earth metal sulphide, more preferably an alkali metal sulphide most preferably sodium sulphide.

In a method according to the invention in which elemental sulphur in alkaline medium is used the alkaline medium is preferably a hydroxide, carbonate and/or alcoholate. More preferably the alkaline medium is selected from alkali metal, alkaline earth metal or ammonium hydroxides, carbonates and alcoholates (preferably water free); most preferably the alkaline medium is selected from alkali metal hydroxides and carbonates and ammonia, especially preferred being sodium or potassium carbonate.

Preferably an amount of 1 mole of sulphur and 1 cation equivalent of alkaline medium are used per mole of compound of formula II and where thioxanthones are formed more sulphur and alkaline medium is used to compensate for the amount of xanthone (up to 20%) that can be formed.

Preferably the method according to the invention is performed in a solvent system, in particular a polar solvent system. Preferred polar solvet systems are those which contain one or more ether, carbonyl, hydroxyl, cyanide, —SO₂ and SO groups. More preferably the solvent system is an aprotic solvet system, most preferably containing one or more solvents selected from dimethylsulphoxide, diethylene glycol, N,N-dimethylacetamide, N-methylpyrrolidone, hexamethylphosphonic acid triamide, sulpholan, 2-methoxyethanol, diethylene glycol monomethylether, diethyleneglycol monoethylether and dimethylformamide of which N,N-dimethylacetamide, N-methylpyrrolidone dimethylsulphoxide and dimethylformamide are especially preferred.

By the term solvent is meant one or more solvents capable of dissolving the reactants at least partially.

The amount of solvent used is not critical nor need it be pure. Preferably however, sufficient is used to make the reactants stirrable at the reaction temperature (e.g. a paste). Preferably 50 to 100 mls of solvent (e.g. dimethylsulphoxide) is used per mole of compound of formula II.

Preferably the method according to the invention is carried out at 20° to 250° C., more preferably 60° to 170° C., most preferably 70° to 150° C., especially 95° to 140° C.

Further, according to the invention there is provided a photopolymerisable composition a photopolymerisable system and a photosensitizing amount of a compound of formula II. Preferably the only photoinitiator present is a compound of formula I and a compound of formula II or a compound of formula II.

Preferably the photosensitizing amount is 0.1 to 10%, more preferably 1 to 5% by weight of the photopolymerisable system present.

Polymerisable systems are in general well known, for example as described in U.S. Pat. Nos. 3,759,807 and 3,876,519; the photopolymerisable systems of these patents are incorporated herein by reference. These are well known in the U.V. curable coating and printing arts. The photopolymerisable systems include unsaturated polymerisable species such as ethylenically unsaturated compounds, e.g. acrylic acid compounds, maleic acid compounds, styrene compounds and homologues thereof as well as epoxide compounds, such as epoxidated linseed oil.

Preferably photopolymerisable compositions according to the invention include one or more amines having at least one α-CH-group present, for example triethylamine or N,N-dimethylaminobenzophenone.

Preferably photopolymerisable compositions of the invention can be polymerised by exposure to U.V. light in the range 250 to 400 nm.

Preferably photopolymerisable compositions according to the invention may include further additives, for example, antioxidants, pigments, fillers. The amounts of these additives used is not critical.

The invention will now be illustrated by the following Examples in which all parts and percentages are by weight and all temperatures are in °C.

Examples 1 to 7 show methods of forming compounds of formula II, which are starting materials in the method of the invention.

EXAMPLE 1

22 g of 4-tert.-octyl-methoxybenzene, 17.5 parts of 2-chloro-benzoylchloride and 0.1 g of ZnCl₂ are stirred in 30 ml of tetrachloroethane at 150° for 3 hours and a brown solution results. 100 ml of water and 2 ml of 2N NaOH solution are added to the brown solution at room temperature, and the mixture is stirred for 15 minutes, the organic phase is then separated and dried and the solvent is distilled off. The residue is distilled under high vacuum (b.p. 225°/0.001 mm) and then recrystallised from hexane. A white product of the formula 1a is obtained,

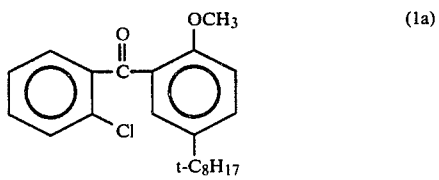

having a melting point of 97°–98° C.

EXAMPLES 2 TO 6

In an analogous manner to that of Example 1 starting from appropriate reactants, compounds of the formula

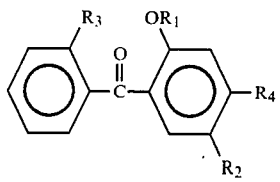

in which R₁ to R₄ are defined in Table 1 below can be prepared.

TABLE 1

| Ex. No. | R₁ | R₂ | R₃ | R₄ |
|---|---|---|---|---|
| 2 | —C₂H₅ | —OC₂H₅ | —Cl | —H |
| 3 | CH₃ | —OCH₃ | —Cl | —H |
| 4 | " | —Cl | —Cl | —H |
| 5 | " | —CH₃ | —Cl | —H |
| 6 | " | —CH₃ | —Cl | —CH₃ |
| 7 | —C₂H₅ | —OC₂H₅ | —OCH₃ | —H |

EXAMPLE 8

9.1 g of 2-methoxy-2'-chloro-5-tert.-butylbenzophenone (m.p. 60-62) is dissolved in 25 ml of dimethylformamide. The clear solution is mixed with 4.15 g of Na₂S.3H₂O at 98°-100° over 1 hour. After a 3 hour reaction at 113°-115° the resulting green mixture is cooled to 50° and then 25 ml of water followed by 30 ml of toluene are added. The toluene phase is separated off at 70° and washed with neutral water and the solvent is then distilled off. The remaining yellow oil is recrystallised twice from methanol. A practically white crystalline compound of the formula 8a

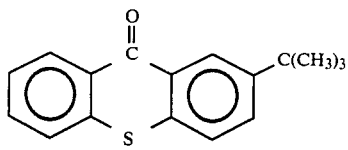

(8a)

results having a melting point of 76°-77° C. and the amount of the corresponding xanthone is about 18% of the yield of thioxanthone.

EXAMPLE 9

13.0 g of 2-methoxy-2'-chloro-5-methyl-benzophenone (m.p. 46° to 47°) are dissolved in 30 ml of dimethylsulphoxide. Whilst stirring 7.26 g of Na₂S.3H₂O are added to the solution at 130° to 138° C. over 40 minutes and a brown mixture results. The mixture is stirred for a further 4 hours at 134°, then cooled to 60° and then 10 ml of methanol followed by 30 ml of water are added; the reaction product then precipitates out. The precipitate is then filtered at 10°, washed with neutral water and recrystallised from methanol in the presence of decolorising carbon. A yellow crystalline compound of the formula 9a

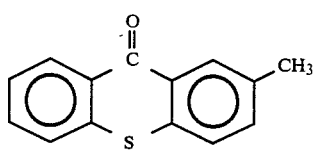

(9a)

results, having a melting point of 121°-124°.

EXAMPLE 10

5.2 g of 2-methoxy-2'-chloro-5-methylbenzophenone are stirred with 14 ml of diethyleneglycol, 1.4 g of sulphur powder and 8.6 g of K₂CO₃ for 1½ hours at 138° to 140°. A brown mixture results. To the mixture 100 ml of water are added at 80° and a thick oil results. The aqueous phase is decanted off and the remaining oil is boiled with 20 ml of methanol, after which the mixture is cooled and the yellow precipitate that results is then filtered. Finally, the product is re-crystallised twice in methanol. The resulting product is of formula Ia defined in Example 9 having about 18% of corresponding xanthone present.

EXAMPLE 11

(a) 152.4 g of 2-chloro-2',5'-diethoxybenzophenone, 32.0 g of elemental sulphur and 151.8 g of K₂CO₃ are added to 120 ml of diethyleneglycol and stirred at 155° for 23 hours. A brown mixture results. This is cooled to 110° and 300 ml of toluene followed by 300 ml of water are added. The aqueous phase is separated off. The toluene phase is washed twice with 150 ml of water and then the toluene is distilled off. The residue is recrystallized from a dioxan-ethanol mixture and the resulting crystalline product is of formula 11a

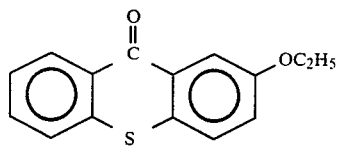

(11a)

having a melting point of 126°-128°. About 18% of the corresponding xanthone is formed.

(b) Similarly, a compound of formula 8a (defined in Example 8) can be prepared by a method analogous to a) above using 63.3 g of 2-chloro-2'-ethoxy-5'-tert.-butylbenzophenone, 9.6 g of sulphur powder and 30.2 g of K₂CO₃ in 24 ml of diethylene gylcols as reactants. 2-tert.-butylthioxanthones having a melting point of 70°-75°, results. (About 18-20% of the corresponding xanthone is formed).

Similarly, 2-isopropylthioxanthone can be prepared by a method analogous to (a) above using 57.8 g of 2-chloro-2'-ethoxy-5'-isopropyl-benzophenone, 12.8 g of sulphur powder, 60.7 g of K₂CO₃ and 48 ml of diethylene glycol as reactants and about 18% of the corresponding xanthone is formed. The melting point of the thioxanthone is 54°-64°.

However by using 33 g of 2-chloro,2'-ethoxy-5'-tert.butylbenzophenone, 260 ml of diethyleneglycol, 70.4 g of sulphur powder and 334 g of K₂CO₃ heated to 155° whilst stirring and then treated according to Example 11a 2-isopropylthioxanthone having a melting point of 74°-76° is obtained having 2-3% xanthone present.

EXAMPLES 12 TO 16

The following compounds can be made by a method analogous to any one of Examples 8 to 11 from appropriate reactants.

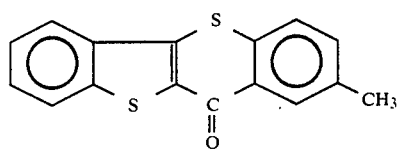

Example 12

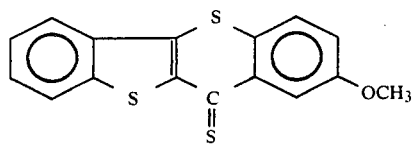

Example 13

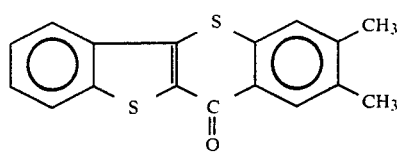

Example 14

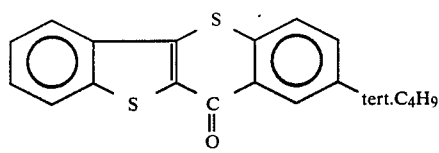

Example 15

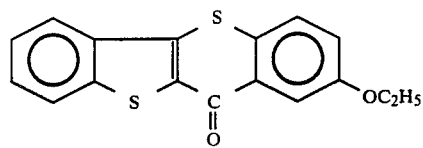

Example 16

EXAMPLE 17

12.0 g of 2,5-diethoxy-2'-methoxybenzophenone (m.p. 101° to 102°) and 5.4 g of Na$_2$S 3H$_2$O are added together in 50 ml of dimethylformamide and are stirred for 6 hours at 114° to 119°. A brown mixture results. To the mixture 20 ml of water are added at 70° after which the mixture is cooled to room temperature and the product precipitates out. The precipitate is filtered, washed with water and then recrystallised from methanol. A white crystalline compound of the formula 17a

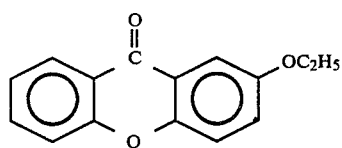
(17a)

results, having a melting point of 126°–127°.

EXAMPLE 18

27.6 g of 2,2'-dimethoxy-5-chlorobenzophenone are dissolved in 70 ml of dimethylformamide. To this solution 14.5 g of Na$_2$S 3H$_2$O are added at 70° whilst stirring. A brown mixture results. The mixture is allowed to react for 3 hours whilst stirring and then the mixture is cooled to 60°. A thick mass results with the product in part precipitating out. At 60° the mixture is diluted with 70 ml of methanol and the precipitate is filtered at 50° C., the precipitate is then washed and the product is recrystallised from methanol-dioxane. The product is a compound of the formula 18a

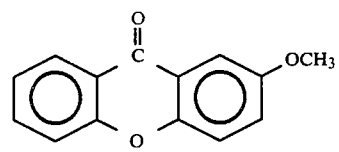
(18a)

having a melting point of 173°–174° C.

EXAMPLE 19

13.6 g of 2,2'-5-trimethoxybenzophenone, 3.5 g of sulphur powder and 21.4 g of K$_2$CO$_3$ are stirred in 35 ml of diethyleneglycol for 4 hours at 134° to 138°. A brown mixture results. To the reaction mass 40 ml of methanol and 40 ml of water are added at 50° and the product precipitates out. The precipitate is filtered at 15° washed with water and dried.

A practically white product of the formula 19a

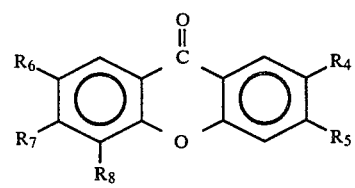
(19a)

having a melting point of 132°–139° C., results. By using 35 ml of 2-methoxyethanol as solvent the same result is obtained.

EXAMPLES 20 TO 28

In an analogous method to that of any one of Examples 17 to 19 starting with suitable reactants the compounds of the formula $$\underset{R_8}{\underset{R_7}{R_6}}\diagdown\!\!\!\!\!\bigcirc\!\!\!\!\!\diagup\overset{\overset{O}{\|}}{C}\diagdown\!\!\!\!\!\bigcirc\!\!\!\!\!\diagup\underset{R_5}{R_4}$$

in which the symbols are defined in Table 2 below, can be prepared.

TABLE No. 2

| Ex. No. | R$_4$ | R$_5$ | R$_6$ | R$_7$ | R$_8$ |
|---|---|---|---|---|---|
| 20 | —OCH$_3$ | —H | —H | —H | —CH$_3$ |
| 21 | " | —H | —H | —CH$_3$ | —H |
| 22 | " | —H | —CH$_3$ | —H | —H |
| 23 | —OC$_2$H$_5$ | —H | —CH$_3$ | —H | —H |
| 24 | —C$_4$H$_9$tert. | —H | —H | —H | —H |
| 25 | —CH$_3$ | —CH$_3$ | —H | —H | —H |
| 26 | " | —CH$_3$ | —CH$_3$ | —H | —H |
| 27 | —C$_8$H$_{17}$tert. | —H | —H | —H | —H |
| 28 | —OCH$_3$ | —H | —C$_4$H$_9$tert. | —H | —C$_4$H$_9$tert. |

EXAMPLES 29 TO 68

Compounds of the formula

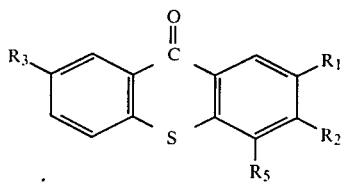

can be prepared by a method analogous to that of any one of Examples 8 to 11 from suitable starting products.

TABLE No. 3

| Ex. No. | $R_1$ | $R_2$ | $R_3$ | $R_5$ |
|---|---|---|---|---|
| 29 | —$CH_3$ | —H | —H | —$CH_3$ |
| 30 | -tert.$C_4H_9$ | —H | —Cl | -tert.$C_4H_9$ |
| 31 | $nC_5H_{11}$ | —H | —Cl | -n-$C_5H$ |
| 32 | tert.$C_8H_{17}$ | —H | —$CH_3$ | -tert.$C_8H_{17}$ |
| 33 | —$CH_3$ | —H | —$CH_3$ | -n-$C_4H_9$ |
| 34 | " | —H | —$C_2H_5$ | -$nC_5H$ |
| 35 | -$nC_4H_9$ | —H | —$C_4H_9$ | —$CH_3$ |
| 36 | cyclopentyl | —H | —H | " |
| 37 | —$CH_2CH_2COOC_2H_5$ | —H | —H | -tert.$C_4H_9$ |
| 38 | " | —H | —Cl | -$nC_5H_{11}$ |
| 39 | —$CH(CH_3)C_6H_5$ | —H | -$nC_3H_7$ | —$CH(CH_3)C_6H_5$ |
| 40 | —$CH_3$ | —H | —H | —$C(CH_3)_2C_6H_3$ |
| 41 | -tert.$C_4H_9$ | —H | —H | " |
| 41a | —$C(CH_3)_2C_6H_5$ | —H | —$CH_3$ | " |
| 42 | cyclohexyl | —H | —Cl | —$CH_3$ |
| 43 | -tert.$C_4H_9$ | —H | —H | sec.$C_4H_9$ |
| 44 | -$nC_8H_{17}$ | —H | —H | -$nC_8H_{17}$ |
| 45 | —$CH_3$ | —$CH_3$ | —H | —H |
| 46 | —Cl | —H | —H | —H |
| 47 | —Br | —H | —$CH_3$ | —H |
| 48 | —$OC_2H_5$ | —H | —H | —H |
| 49 | —$OC_4H_9$—n | —H | —H | —H |
| 50 | —$C_2H_5$ | —H | —H | —H |
| 51 | -$nC_4H_9$ | —H | —$CH_3$ | —H |
| 52 | -$nC_3H_7$ | —H | —H | —H |
| 53 | -i-$C_3H_7$ | —H | —Cl | —H |
| 54 | -tert.$C_4H_9$ | —H | —Cl | —H |
| 55 | -n-$C_5H_{11}$ | —H | —H | —H |
| 56 | cyclohexyl | —H | —H | —H |
| 57 | —Cl | —H | —Cl | —H· |
| 58 | —$CH_3$ | —H | tert.$C_4H_9$ | —H |
| 59 | —$C_2H_5$ | —H | —H | —$C_2H_5$ |
| 60 | —$CH_3$ | —H | —H | —$CH_3$ |
| 61 | -$nC_9H_{19}$ | —H | —H | —H |
| 62 | -$nC_{12}H_{25}$ | —H | —Cl | —H |
| 63 | —$CH_3$ | —$CH_3$ | —Cl | —H |
| 64 | —$OCH_3$ | —H | —Cl | —H |
| 65 | —$CH_3$ | —$CH_3$ | —H | —H |
| 66 | -tert.$C_8H_{17}$ | —H | —H | —H |
| 67 | —$OC_2H_5$ | —H | —H | —H |
| 68 | -tert.$C_4H_9$ | —H | —H | —$CH_3$ |

APPLICATION EXAMPLE A

A mixture of 60 g of a prepolymer of the formula 33a

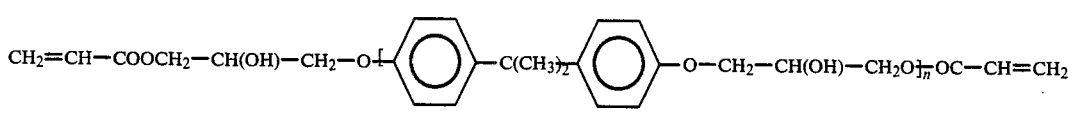

having a viscosity of c. 9000 poise (at 77°) (described in U.S. Pat. No. 3,713,864), 35 g of pentaerithritoltetraacrylate and 40 parts of $TiO_2$ (Chronos RN 63) are mixed homogeneously on a 3 roller mill. To this mixture 2.5% by weight of the compound of formula Ia defined in Example 1 are added. The mixture is homogenised in a mixer with 2×25 revs. The resulting mixture is separated into two parts. One part is applied with a spatula onto paper for artificial prints with a thickness of 3–5μ and the other part is applied with a doctor blade on aluminium foil with a thickness of 20μ.

Both films are hardened in a minicure apparatus (Primarc) with an Hg medium power lamp (80 W/cm) at high speed and dried to a non-sticky film.

APPLICATION EXAMPLE B

100 Parts of a photopolymerisable system of 67 parts of a polyester (prepared from maleic acid anhydride, phthalic acid anhydride and propane-1,2 diol) and 33 parts of styrene are homogenised with 38 parts of $TiO_2$ (Chronos RN 63) in a roller mill. To this mixture 3 parts of the compound of formula Ia (defined in Example 1) and 3.3 parts of p-dimethylaminobenzoic acid ethyl ester are added and then further treated accordingly to Application Example A.

In analogous manner any one of the compounds of Examples 2 to 68 can be used in place of that of Example 1 in Examples A or B.

What we claim is:

1. A method for preparing a compound of formula I

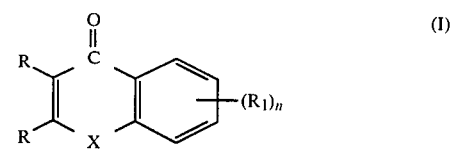

in which
X is O or S;
both groups R together with the two carbon atoms to which they are attached form a fused aromatic group;
$R_1$ is selected from $C_{1-18}$alkyl,
cyclo $C_{5-7}$alkyl, phenyl $C_{1-4}$alkyl, $C_{1-4}$alkoxy $C_{1-4}$alkyl, $C_{1-4}$alkoxycarbonyl $C_{1-4}$alkyl, $C_{1-4}$alkylcarbonyloxy $C_{1-4}$alkyl, $C_{1-8}$alkoxy, phenyl $C_{1-4}$alkoxy and halogen; and
n is 0, 1, 2 or 3 comprising reacting a compound of formula II

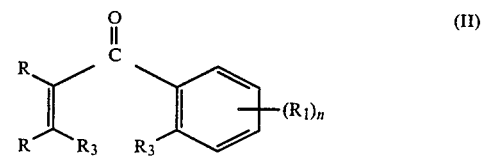

where R, $R_1$ and n are defined above and where each $R_3$, independently, is $C_{1-12}$alkoxy or one $R_3$ is $C_{1-12}$alkoxy and the other $R_3$ is halogen, with elemental sulphur in an alkaline medium, a metal sulphide or a metal hydrosulphide, provided that when X in formula I is S, then one $R_3$ in formula II is $C_{1-12}$alkoxy and the other $R_3$ is halogen.

2. A method according to claim 1 for preparing a compound of formula Ia

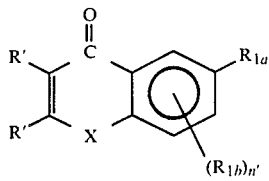  (Ia)

in which

X is O or S, $R_{1a}$ is hydrogen, $C_{1-18}$alkyl, phenyl $C_{1-3}$-alkyl, cycloC-$_{5-7}$alkyl, $C_{1-8}$alkoxy, benzyloxy, $C_{1-3}$alkoxycarbonylethyl or halogen;

$R_{1b}$ is $C_{1-8}$alkyl, $C_{1-8}$alkoxy or halogen;

n' is 0, 1 or 2;

both groups R' together with the two carbon atoms to which they are attached form a group of formula (a), (b), (c), (d) or (e)

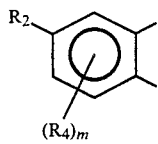  (a)

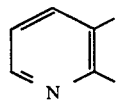  (b)

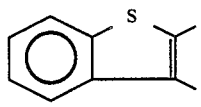  (c)

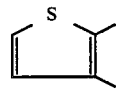  (d)

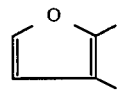  (e)

where $R_2$ is hydrogen, $C_{1-4}$alkyl, $C_{1-4}$alkoxy or halogen;

$R_4$ is $C_{1-4}$alkyl or halogen provided not more than one $R_4$ group is halogen; and m is 0, 1, 2 or 3, comprising reacting a compound of formula IIa

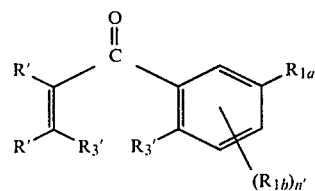  (IIa)

in which R', $R_{1a}$, $R_{1b}$ and n' are defined above and each $R_3$, independently, is $C_{1-6}$alkoxy or one $R_3$ is $C_{1-6}$alkoxy and the other $R_3$ is Cl or Br, with elemental sulphur in alkaline medium, a metal sulphide or a metal hydrosulphide, provided that when X in formula Ia is S, then one $R_3$ in formula IIa is $C_{1-6}$alkoxy and the other $R_3$ is Cl or Br.

3. A method according to claim 1 in which the compound of formula II is reacted with elemental sulphur in alkaline medium or a metal sulphide.

4. A method according to claim 1 in which the reactants are in a solvent system.

5. A method according to claim 1 in which the reaction is carried out at 20° to 250° C.

6. A method according to claim 2 in which the compound of formula IIa is reacted with elemental sulfur in alkaline medium or with a metal sulphide.

7. A method according to claim 2 in which the alkaline medium is a hydroxide, carbonate or alcoholate of an alkali metal, alkaline earth metal or ammonium and the metal sulphide is an alkali metal or alkaline earth metal sulphide.

8. A method according to claim 6 in which the alkaline medium is a hydroxide, carbonate or alcoholate of an alkali metal, alkaline earth metal or ammonium and the metal sulphide is an alkali metal or alkaline earth metal sulphide.

9. A method according to claim 4 in which the solvent system is a polar solvent system.

10. A method according to claim 3 in which the reaction is effected in a polar solvent system.

11. A method according to claim 6 in which the reaction is effected in a polar solvent system.

12. A method according to claim 7 in which the reaction is effected in an aprotic solvent system.

13. A method according to claim 8 in which the reaction is effected in an aprotic solvent system.

14. A method according to claim 8 in which the reaction is effected in a solvent selected from the group consisting of dimethylsulphoxide, diethylene glycol, N,N-dimethylacetamide, N-methylpyrrolidone, hexamethylphosphonic acid triamide, sulpholan, 2-methoxyethanol, diethylene glycol monomethyl ether, diethylene glycol monoethyl ether and dimethylformamide.

15. A method according to claim 2 in which the reaction is carried out at a temperature of 20° to 250° C.

16. A method according to claim 6 in which the reaction is carried out at a temperature of 60° to 170° C.

17. A method according to claim 7 in which the reaction is carried out at a temperature of 60° to 170° C.

18. A method according to claim 12 in which the reaction is carried out at a temperature of 70° to 150° C.

19. A method according to claim 13 in which the reaction is carried out at a temperature of 70° to 150° C.

20. A reaction according to claim 14 in which the reaction is carried out at a temperature of 95° to 140° C.

* * * * *